(12) United States Patent
Li (10) Patent No.: US 8,271,296 B2
(45) Date of Patent: Sep. 18, 2012

(54) SITE EFFECTIVENESS INDEX AND METHODS TO MEASURE AND IMPROVE OPERATIONAL EFFECTIVENESS IN CLINICAL TRIAL EXECUTION

(76) Inventor: Gen Li, East Lyme, CT (US)

( * ) Notice: Subject to any disclaimer, the term of this patent is extended or adjusted under 35 U.S.C. 154(b) by 233 days.

(21) Appl. No.: 12/729,366

(22) Filed: Mar. 23, 2010

(65) Prior Publication Data

US 2010/0250273 A1   Sep. 30, 2010

Related U.S. Application Data

(60) Provisional application No. 61/163,528, filed on Mar. 26, 2009.

(51) Int. Cl.
*G06Q 10/00* (2012.01)
*G06Q 50/00* (2012.01)
(52) U.S. Cl. ............................ 705/2; 705/3; 600/300
(58) Field of Classification Search .................. 705/2–3; 600/300
See application file for complete search history.

(56) References Cited

U.S. PATENT DOCUMENTS

| | | | |
|---|---|---|---|
| 2003/0208378 A1 | 11/2003 | Thangaraj et al. | |
| 2005/0182663 A1* | 8/2005 | Abraham-Fuchs et al. | ...... 705/3 |
| 2006/0282244 A1 | 12/2006 | Chotai et al. | |
| 2007/0100885 A1* | 5/2007 | Sumino et al. | ............. 707/104.1 |
| 2007/0250429 A1 | 10/2007 | Walser et al. | |
| 2010/0114594 A1* | 5/2010 | Schultz | ............................ 705/2 |

OTHER PUBLICATIONS

Getz, The Elusive Sponsor-Site Relationship, Feb. 2009, Applied Clinical Trials, pp. 38-40.*

* cited by examiner

*Primary Examiner* — Luke Gilligan
(74) *Attorney, Agent, or Firm* — Law Offices of Albert Wai-Kit Chan, PLLC (57) ABSTRACT

This invention provides a method of improving operational effectiveness in a clinical trial, the method comprises the steps of: obtaining historical clinical trial operation data for a disease condition; normalizing data from different clinical trials; grouping different clinical trials into groups; and calculating Site Effectiveness Index (SEI), wherein the SEI is useful for improving operational effectiveness in a clinical trial. In one embodiment, using the method disclosed herein would result in reducing the cost for the clinical trial.

9 Claims, 6 Drawing Sheets

SITE EFFECTIVENESS INDEX AND METHODS TO MEASURE AND IMPROVE OPERATIONAL EFFECTIVENESS IN CLINICAL TRIAL EXECUTION

CROSS-REFERENCE TO RELATED APPLICATIONS

This application claims benefit of U.S. Ser. No. 61/163,528, filed Mar. 26, 2009. The entire content and disclosure of the preceding application is incorporated by reference into this application.

FIELD OF THE INVENTION

This invention relates generally to methods of improving operational effectiveness in clinical trial execution.

BACKGROUND OF THE INVENTION

Nothing in any other industry quite compares to the pharmaceutical industry's clinical development process. In 2007, $28 billion dollars were spent on drug development. Nowadays a single clinical trial can be capital intensive (up to $500 million), with massive geographic coverage (as many as 53 countries), long duration (five years or longer), and enroll a large number of patients (20,000- to 50,000-patient trials are no longer rare).

A median Phase III clinical trial involves about 800 patients, 50 investigator sites, and two years (700 days) from First Subject First Visit (FSFV) to Last Subject Last Visit (LSLV). Add in the costs of per-patient medical procedures, drug supplies, laboratory work, and sponsor's personnel, and a median-sized clinical trial can cost upwards of $25 million, about $36,000 every single day.

Clearly clinical trials are extremely important to the pharmaceutical industry both as the source for clinical data and as an enormous cost center. And the patient enrollment phase of a trial is the most variable part of the process—that is, the spot where we could most reasonably expect to drive down costs. But we still lack a fundamental understanding of patient enrollment as a business process. While many companies are attempting to manage trials better, it is not surprising to see that their approaches, even those of established industry experts, lack in structure and objectivity and occasionally make things worse—for example, by making false assumptions about who has final responsibility for recruiting patients.

There are ongoing and intensive efforts being made in drug development organizations around the world to improve the efficiency and effectiveness in clinical trial execution. There are many examples of successfully executed clinical trials based on better understanding and better planning of trials by those more experienced and more knowledgeable professionals. Successful clinical trials sometimes also resulted from a better designed and executed business processes by some of the drug development organizations. Clearly, we are also collectively benefiting from progresses being made in information technology. However, the learning and success in drug development operations are isolated, subjective, and difficult to be institutionalized for cross fertilization. Thus, there is a need to develop new methodology that would enable us to quantitatively identify and realize opportunities for improvement in clinical trial execution.

SUMMARY OF THE INVENTION

This invention connects known key operational variables mathematically in clinical trial execution through Site Effectiveness Index (SEI). These key variables include, but are not limited to milestones such as first subject first visit (FSFV) and last subject first visit (LSFV) at clinical trial level, as well as the date a site opened for enrollment, the date a site closed for enrollment; targeted/actual number of patient enrollment; maximum number of investigator sites activated and opened for enrollment in the duration of patient enrollment from FSFV to LSFV.

The present invention provides a method of calculating and utilizing SEI to improve operational effectiveness in clinical trial execution, resulting in financial savings and cycle time reductions. Moreover, replacing a nominal patient enrollment rate as defined by number of patients enrolled per deployed site per month by SEI and a true site enrollment rate would also enable us to quantify improvement opportunities in site activation and site selection based on historic performance.

DETAILED DESCRIPTION OF THE INVENTION

Patient enrollment, at its simplest, consists of three phases: site selection, site activation, and patient recruitment. As used herein, site selection is the process of identifying a sufficient number of good-quality investigators to conduct the trial. This is one of the greatest challenges in clinical trial execution. You need to find someone with considerable medical skills, commitment to research, good facilities, willingness to fill in endless forms, and last but not least, access to patients who fit the patient selection standard and will agree to enroll.

As used herein, site activation refers to steps taken to bring a site to the point where it is ready to recruit patients, and it consists of a variety of tasks including: negotiate a financial contract; gain approval from Institutional Review Board (IRB) or, in Europe, Ethics Board (EB); provide clinical supplies; obtain other documents from site (CV, financial disclosure, etc).

Though the two activities are entirely different in content at investigator site level, patient recruitment generally occurs simultaneously with site activation at clinical trial level. This is partly because clinical trial teams are often not sure they have an adequate number of sites until they come very close to their enrollment target. As a result, they tend to keep activating sites until enrollment is almost complete. It is also true that sites are being activated at different point of time because of factors contributed by sites such as frequency of IRB/EB meetings, experience of investigator and clinical research coordinator, etc.

For many different reasons, drug development organizations often rush to execution of clinical trials, and try to solve the problems along the way as they arises. Sometimes the problems are too difficult to overcome due to operational causes, which lead to failure of trials.

Simple forms of business practices can be put in place with an aim for achieving better results. For example, going broader geographic coverage (more countries) in a hope to have better access to relevant patients may improve performance of individual sites. People also generally believe that increased number of participating sites (N) can mend the performance shortfalls from individual sites, therefore reducing enrollment cycle times. However, without having a clearly defined mathematic relationship to look into the picture in its entirety, and lack of benchmark data to help understand what is possible, what is impossible, as well as the limitations in each dimension of these variables, these business practices often lead to unwanted consequences. For example, same number of participating sites from more countries may stretch supply chain management organizations, increase complexity in dealing with local regulatory authorities, and insufficient capacity in local subsidiaries. While mathematically more sites can shorten enrollment cycle times, the limitation lies in higher portion of the resources being spent on site activation related activities, not on activities useful for improving site performance in patient enrollment.

Traditionally, certain criteria were used to describe project team performance. For example, enrollment rate as defined by number of patient enrolled per site per month. This term is a mixed bag, however, as it actually included both performance of participating sites and how effectively the participating sites were utilized by the organization running the trial. Performance of participating sites is determined by factors such as experience of principal investigator and clinical research coordinator from the sites, infrastructural factors such as frequency of IRB meetings (EC in Europe). Effective utilization of participating sites, on the other hand, is determined by internally defined business process from the organization that runs the trial.

Every single clinical trial has its distinct characteristics with variables such as medicines being evaluated, targeted disease condition(s), stage of development, the organization sponsoring the clinical trial, the organization executing the clinical trial (when it is outsourced), design of the trial, size of the trial (targeted enrollment), etc. This list of variables can easily exceed 100! It is therefore not possible to compare even two trials side to side. Luckily, not all the variables are all independent. Seeking and establishing relationships among these variables can dramatically simplify the picture. Also, structural similarities among major categories of clinical trials can help us to better answer often very challenging questions.

In addition to clearly defined mathematic relationship for key variables in clinical trial execution, relevant historical data from the industry are also required for identifying and defining opportunities with well defined boundaries for improvement. There are intensifying efforts in the industry to better use benchmark data for this purpose. Generally speaking, however, benchmark exercise in drug development operations as of today lacks comprehensiveness, timeliness, specificity, and objectiveness.

Application of Site Effectiveness Index and the methods disclosed herein require drug development organizations to take a more pragmatic approach, and to do a better job in planning by focusing on study start up process, including site activation and site selection.

The Site Effectiveness Index disclosed herein would help us to establish relationship among factors such as enrollment cycle time at clinical study (trial) level, enrollment cycle time at investigator site (site) level, number of sites deployed for a specific clinical trial, the quality of the sites being selected as being measure by number of patients enrolled in defined period of time, and how effectively all the deployed sites are utilized.

In one embodiment, Site Effectiveness Index (SEI) is used to measure operational effectiveness in site activation in executing clinical trials, which covers the entire study start up. In one embodiment, SEI equals to percentage of peak enrolling sites opened for patient enrollment in the duration of clinical trial enrollment, from first subject first visit (FSFV) to last subject first visit (LSFV); and for each activated participating site, SEI equals to average percentage of site enrollment cycle time over clinical trial enrollment cycle time. In general, SEI does not apply to the following situations: Phase I studies; studies with less than certain number of sites; and studies with no time sensitivity. It is generally true that cluster of clinical trials for certain disease conditions with longer enrollment durations tend to have higher SEI value than those trials with shorter enrollment durations.

Site Effectiveness Index (SEI) is potentially disease indication dependent, as some indications/trials require unique steps in site activation. In another embodiment, SEI is potentially sponsor/executer dependent, as business processes differ among business entities conducting the trials. In another embodiment, SEI is potentially time dependent, as disease epidemic evolve, and competitive landscape evolve. In yet another embodiment, SEI is potentially scale dependent, as operational complexity increases accordingly.

As used herein, Site Effectiveness Index (SEI) is defined as:

Eti: The time (date) site i closed for patient enrollment $$SEI = \frac{\int_{i=1}^{N}(Et_i - St_i)}{(Et_s - St_s) \times N}$$

Sti: The time (date) site i opened for patient enrollment

N: maximum number of sites opened for enrollment in the duration of patient enrollment at the study level Ets: The time (date) clinical study (trial) closed for patient enrollment Sts: The time (date) clinical study (trial) opened for patient enrollment As used herein, enrollment cycle time is driven by successful study start up process and the performance of the sites selected. In one embodiment, a mathematical expression of Enrollment Cycle Time is:

Enrollment Cycle Time=Total Enrollment/(Enrollment Rate)(Number of enrolling sites), wherein the enrollment rate is related to site selection (performance), and number of enrolling sites is related to study startup (process).

In one embodiment, the relationship of Site Effectiveness Index (SEI) with other variables such as Enrollment Cycle Time can be described as:

Enrollment Cycle Time=Total Enrollment/(Average Site Enrollment Rate)(SEI×$N$)

Where Average Site Enrollment Rate (ASER) is defined as:

$$ASER = \frac{TE}{\int_{i=1}^{N}(Et_i - St_i)}$$

wherein TE is Total Enrollment. When it is in the planning stage, TE is targeted patient enrollment. When historical data are being evaluated, TE is the actual number of patient enrolled in a clinical trial.

ASER can be used to measure overall quality of site selection for the entire pool of investigators sites used in a clinical trial, or any number of a subset of sites in a clinical trial. It can also be used to indicate desired site performance when a clinical trial is in the planning stage.

Figure 1:
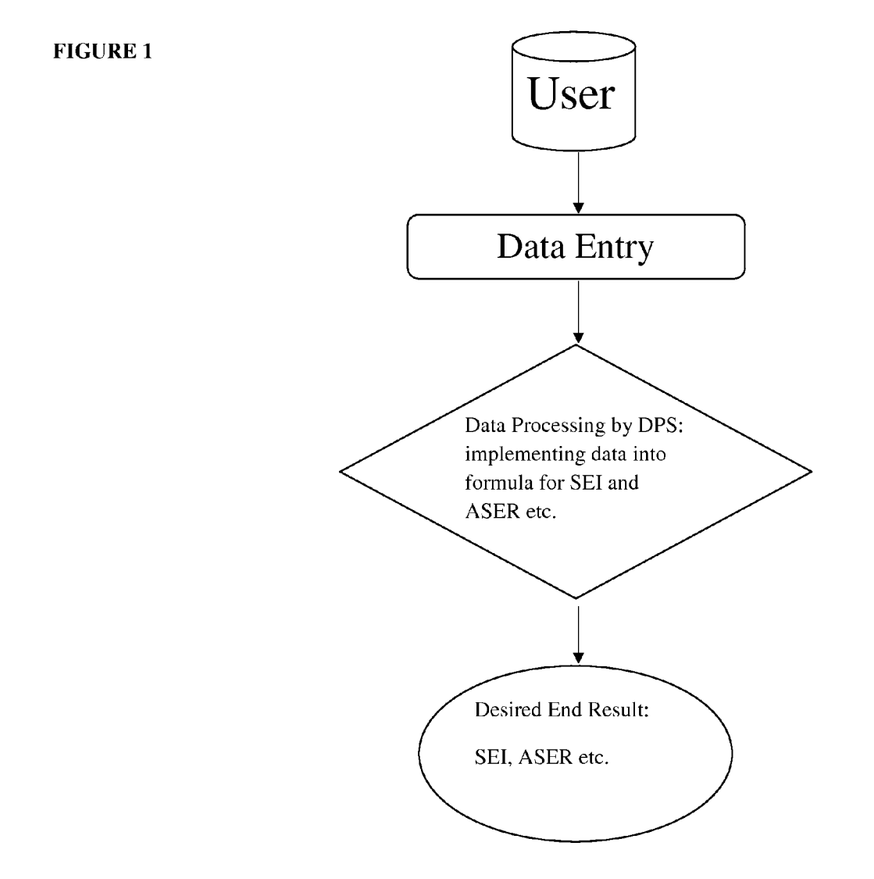
FIG. 1 shows a Computer Based Clinical Data Processing System (DPS).

The present invention provides a computer-assisted method of improving operational effectiveness in a clinical trial. In one embodiment, the method involves calculation and data analysis performed by a computer-based calculating system such as a computer or other similar electronic calculating devices well-known and routinely used in the art. For example, data analysis can be performed by a Computer Based Clinical Data Processing System (DPS) (FIG. 1). Data analysis and the formula for calculating SEI and ASER can be implemented into the software component of the DPS. The DPS may be implemented on computers or other electronic devices. In one embodiment, the DPS can have a user interface that requires users to input the relevant variables into the system. Data entered by the user will be processed by the computer to produce the desired end results such as SEI and ASER etc.

In one embodiment, the method disclosed herein comprises the steps of: inputting historical clinical trial operation data for a disease condition into a computer-based calculating system; normalizing data from different clinical trials; calculating Site Effectiveness Index (SEI); grouping different clinical trials into groups; and analyzing and identifying sponsor(s) with desirable SEIs and identifying underlying best practices. Various factors that may impact SEI are analyzed; such factors include, but are not limited to, inclusion and exclusion criteria for patient recruitment, drug candidate formulation, drug candidate molecular properties etc. In another embodiment, time trend for the clinical trial in planning may also be analyzed and identified. Planning and executing clinical trials based on SEIs maximized from the above described steps is expected to achieve operational effectiveness with quantifiable cost savings and cycle time reduction.

In one embodiment, the method disclosed herein utilizes historical data comprising parameters such as number of investigator sites open for patient enrollment, design of the study, key inclusion exclusion criteria, targeted number of patient enrollment, company sponsoring the clinical trial, intervention(s), disease condition(s), and protocol identification(s) from sponsor(s).

In one embodiment, the data are normalized by expressing enrollment time as percentage of total enrollment cycle time. In another embodiment, the data are normalized by expressing number of sites activated for enrollment as percentage of maximum number of sites open for enrollment.

In one embodiment, data of different clinical trials are grouped according to number of patients enrolled per deployed site per month.

In one embodiment, the Site Effectiveness Index (SEI) is defined as $$SEI = \frac{\int_{i=1}^{N}(Et_i - St_i)}{(Et_s - St_s) \times N}$$

wherein $Et_i$ is the date site i closed for patient enrollment; $St_i$ is the date site i opened for patient enrollment; N is maximum number of sites opened for enrollment in the duration of patient enrollment at the study level; $Et_s$ is the date clinical trial closed for patient enrollment; and $St_s$ is the date clinical trial opened for patient enrollment.

In another embodiment, the SEI is related to Enrollment Cycle Time as follows: Enrollment Cycle Time=Total Enrollment/(Average Site Enrollment Rate)(SEI×N), wherein the Average Site Enrollment Rate has been defined above.

In one embodiment, the SEI is calculated by measuring an area covered by a site activation curve, as percentage of a rectangle area, where one side equals to the enrollment duration, the other side equals to the maximum number of sides open for enrollment.

The invention being generally described, will be more readily understood by reference to the following examples which are included merely for purposes of illustration of certain aspects and embodiments of the present invention, and are not intended to limit the invention.

EXAMPLE 1

Figure 2:
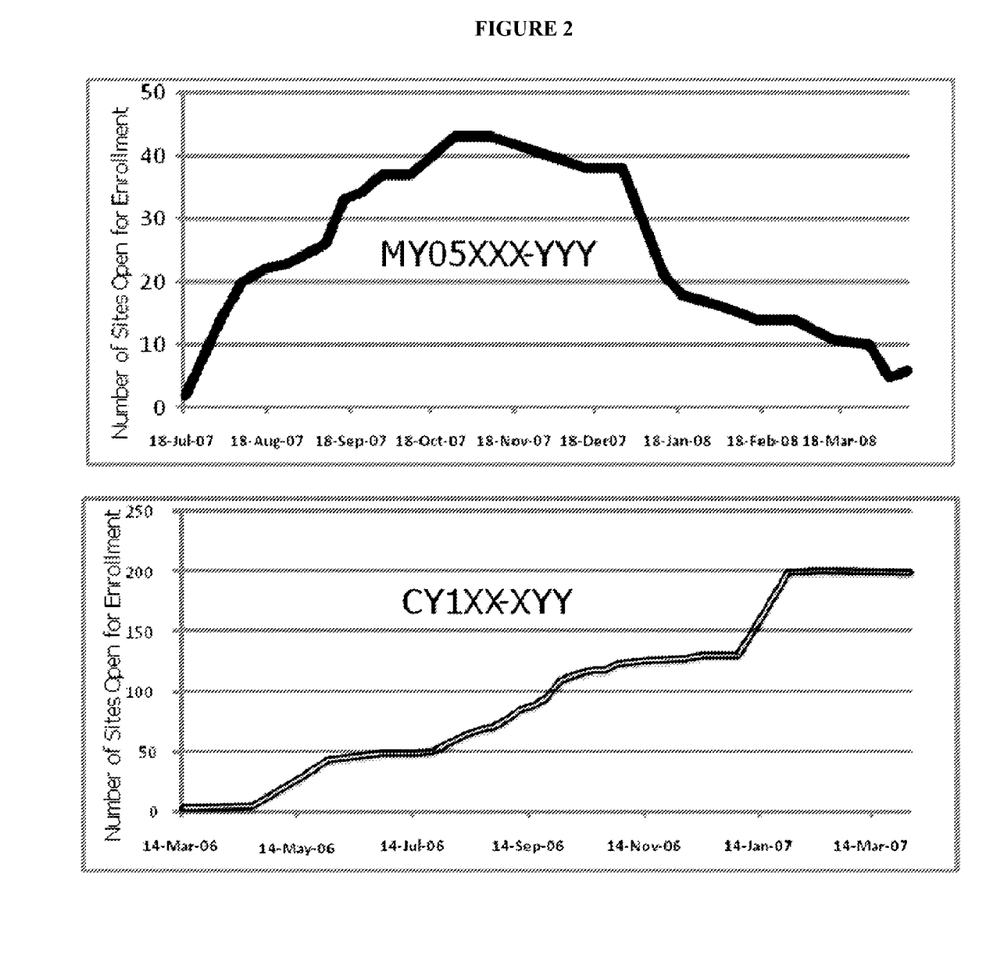
FIG. 2 shows the site activation curves for two different clinical trials (MY05XXX-YYY and CY1XX-XYY).

Define Operational Boundaries and Quantitative Operational Improvement Opportunities Step 1: Use a protocol synopsis of a planned clinical trial as a guidance to identify clinical trials in similar disease condition. Extract from a database historical operations data, including number of investigator sites open for patient enrollment at different point of time along the timeline between first subject first visit (FSFV) and last subject first visit (LSFV), and last subject last visit (LSLV), design of the study, key inclusion exclusion criteria, targeted number of patient enrollment, milestones including FSFV and LSFV, the company sponsoring the clinical trial, intervention(s), disease condition(s), and protocol identification(s) from sponsor(s). In the present example, diabetes is chosen as the disease condition, and the PhESiTM database is the source for historical operations data. Two examples of site activation curve charts are shown in FIG. 2.

Figure 3:
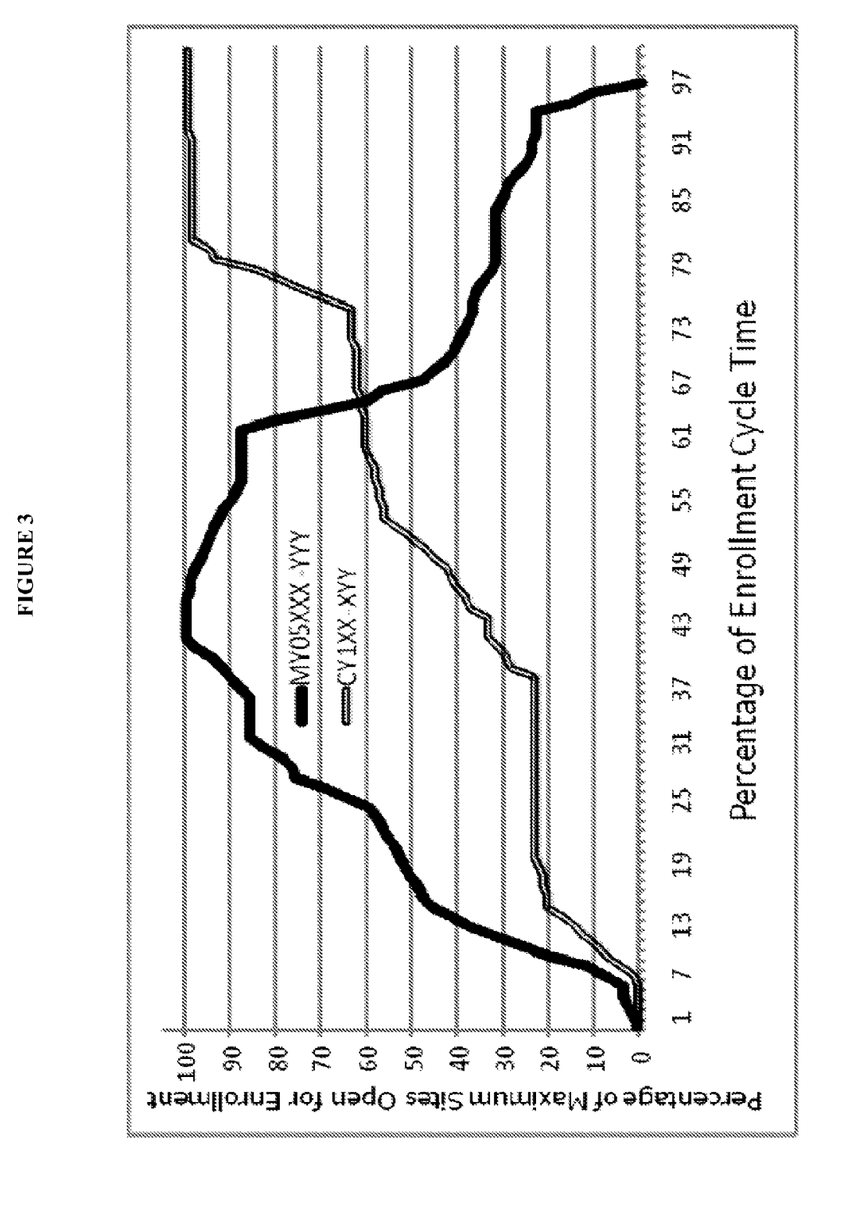
FIG. 3 shows data normalization of the two clinical trials (MY05XXX-YYY and CY1XX-XYY). The x-axis is expressed as percentage of the time duration from the first subject first visit (FSFV) to last subject first visit (LSFV), whereas the y axis is expressed as percentage of maximum number of sites opened for patient enrollment.

Step 2: Data normalizations are performed to make variables from different clinical trials comparable as shown in FIG. 3. In one embodiment, all the enrollment time points were expressed as percentage of total enrollment cycle time, from first subject first visit (FSFV) to last subject first visit (LSFV). All the number of sites activated for enrollment is expressed as percentage of maximum number of sites open for enrollment in the duration of patient enrollment. This step allows unlimited number of curves, each curve represents one clinical trial, in a single chart for comparison.

Step 3: Simple descriptive statistical method can be used to group the curves generated in Step 2. In this particular example, all the curves were sorted by number of patients enrolled per deployed site per month. Those trials with 0.6 patients per deployed site per month were in "top" group. Those trials with 0.3 patients per deployed site per month were in "bottom" group. All the other trials in between belong to a third group. According to the sample size and business need to understand the level of details, clinical trials of interest can be grouped into a number of groups such as two, three, five groups, etc. Top and bottom groups were further analyzed to establish operational boundaries, either by using abstractive group data, or use representative trials from the two groups. FIG. 3 shows two representative trials from the top group and the bottom group. Curves can also be grouped by the values of ASER, or values of SEI, or the product of ASER and SEI, or other parameters relevant to the business issues being analyzed.

Defining operational boundaries usually starting from median values of selected parameters such as SEI, ASER. While examples of clinical trials selected for analysis are with the same disease condition, many other factors need to be assessed vigorously to ensure comparability. Other than disease conditions, examples of these factors include, but are not limited to, patient recruitment inclusion criteria and exclusion criteria, drug candidate formulation, and molecular properties of drug candidate etc.

Table 1 shows a listing of the clinical trial mandatory parameters to ensure the comparison of operational deliverable parameters is legitimate. Such parameters include disease indication (Type II Diabetes in this case), stage of drug development (Phase III in this case), targeted patient enrollment (700 and 565 in the present example).

TABLE 1

Clinical Trial Parameters

| Parameters | Clinical Trials | |
|---|---|---|
| | MY05XXX-YYY | CY1XX-XYY |
| Phase | III | III |
| Indication | T2DM | T2DM |
| Enroll Target | 700 | 565 |
| Enroll Duration (days) | 280 | 423 |
| Sites Activated | 44 | 204 |
| Nominal Enroll Rate (patients/deployed site/month) | 1.67 | 0.19 |

Step 4: Site Effectiveness Index can be calculated by measuring the area covered by the site activation curve as percentage of the area as defined by maximum number of sites open for enrollment times clinical trial enrollment duration. In the present example, trial MY05XXX-YYY has an SEI of 0.55, whereas trial CY1XX-XYY has an SEI of 0.45. This helps to define the boundary of opportunity in site activation improvement.

In conjunction with other operational variables, site enrollment rates can also be calculated to identify potential opportunities in selecting better performing sites for this particular disease condition. For example, for each participating sites which were activated and open for enrollment, actual number of patients enrolled in the entire clinical trial, divided by the sum of enrollment duration from each site (expressed by total number of months) would result in an average number of patient enrolled per site per month. In the present example, trial MY05XXX-YYY has an average site enrollment rate (ASER) of 3 patients per site per month, and trial CY1XX-XYY has an average site enrollment rate (ASER) of 0.5 patients per site per month.

Generally speaking, any number of sites from a single clinical trial can be pooled to calculate their collective ASER by using the method described above. Practically, there is a "warm up" period for an investigative site to go into steady enrollment of patients. High performing sites are usually capable of going into steady enrollment quickly, with a relatively shorter "warm up" period. On the other hand, there are cases where not enough number of investigative sites were used, which requires more sites to be added in the middle of clinical trial execution. Those added sites were often being asked to close before they complete "warm up" period, when the clinical trial reached planned enrollment target. The ASER for these added sites, in this situation under-estimate their true enrollment capability.

As shown in Table 1, clinical trials with similar enrollment target (700 vs. 565 patients) may be set up differently in terms of enrollment duration and the number of sites activated. Differences in enrollment duration and the number of sites activated would translate into saving or expenses of millions of dollars When Site Effectiveness Index being maximized, the patient enrollment capacities of all the investigative sites being used in a clinical trial is being utilized to the highest possible percentage, which would potentially reduce total number of sites needed for the clinical trial, or enroll targeted number of patients in shorter period of time, or achieve combination of both. Number of sites is a key driver to costs in clinical trials, and enrollment cycle time is both a cost driver and to determine time to market for the drug under development.

The method described in Step 1 to Step 5 covers in detail the utilization of disease specific historic data. Following the method described herein, one of ordinary skill in the art would also readily perform the same analysis to understand potential SEI dependency on time, or on sponsor/executor (in case of trial being outsourced) instead of disease conditions (Type 2 diabetes in this example). Clinical development organizations around the world are seeking opportunities to improve clinical trial deliverables, as the result of that, one may observe an improving trend for a specific type of clinical trials over time. Contrary to that, there is possibility of deteriorating trend in SEI over time, contributed by factors such as competition, or changed disease dynamic because of major breakthrough in new therapies. A time dependency analysis would help to proactively identify potential opportunities or challenges, and align resources accordingly to capitalize the opportunity or deal with the challenge. Similarly, some of the sponsors may execute certain type of clinical trials with significantly better SEIs. Sponsor specific analysis would allow us to identify the root causes therefore specific opportunities to improve.

EXAMPLE 2

Measuring Site Activation

There are different ways to measure effectiveness in trial site activation. The cycle time of site activation is one. Site activation starts from the time the first site is activated or initiated, and ends when the last site is activated. The less time between the first site activation and the last site activation, the more effective the overall activation process will be. As in the process of enrollment, site activation cycle times depend on many variables, making it difficult to compare one clinical trial against another.

Site Effectiveness Index (SEI) disclosed herein defines how effectively selected sites in a clinical trial are utilized. There are two ways to measure SEI. One is the percentage of selected sites open for enrollment over the duration of the enrollment cycle time. Another is from a single participating site perspective; its percentage of time open for enrollment compared to the overall clinical trial enrollment duration. As a percentage, SEI is always represented as a number larger than zero and smaller than one. A real-world case study will help explain the concept of SEI.

Figure 4:
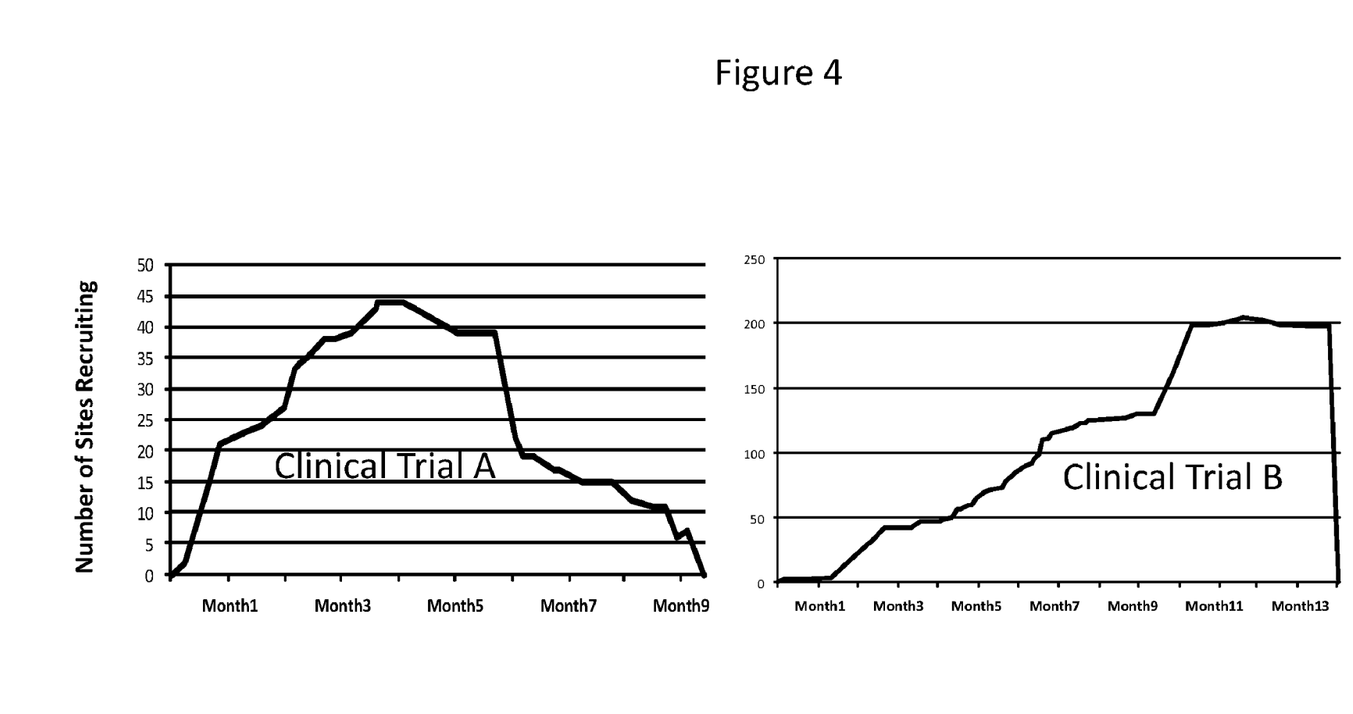
FIG. 4 shows comparison of Clinical Trials A and B on site activation curves

As shown in FIG. 4, Clinical Trial A and Clinical Trial B are two Phase III metabolic disease clinical trials in the same indication with the same design, sponsored by two different companies. By drawing two charts, one can see the site activation curves for the two clinical trials along the time line. Clinical Trial A activated 44 sites while Clinical Trial B initiated a total of 204 sites. It took less than four months for Clinical Trial A to reach the peak of site activation (i.e., for all 44 sites to be actively recruiting), while it took about 10 months for Clinical Trial B to get its selected sites up and running.

Because Clinical Trial A and Clinical Trial B are similar in many ways, any deeper insight requires a methodology to compare the two trials. To achieve that, the X axis was defined as the percentage of enrollment duration and the Y axis as the percentage of maximum number of sites activated, instead of the actual number of sites activated (see FIG. 5). By doing that, one can see that area underneath the black colored line (Clinical Trial A) covers more than half of the chart area, and the area underneath the red colored line (Clinical Trial B) covers less than half of the chart area.

Figure 5:
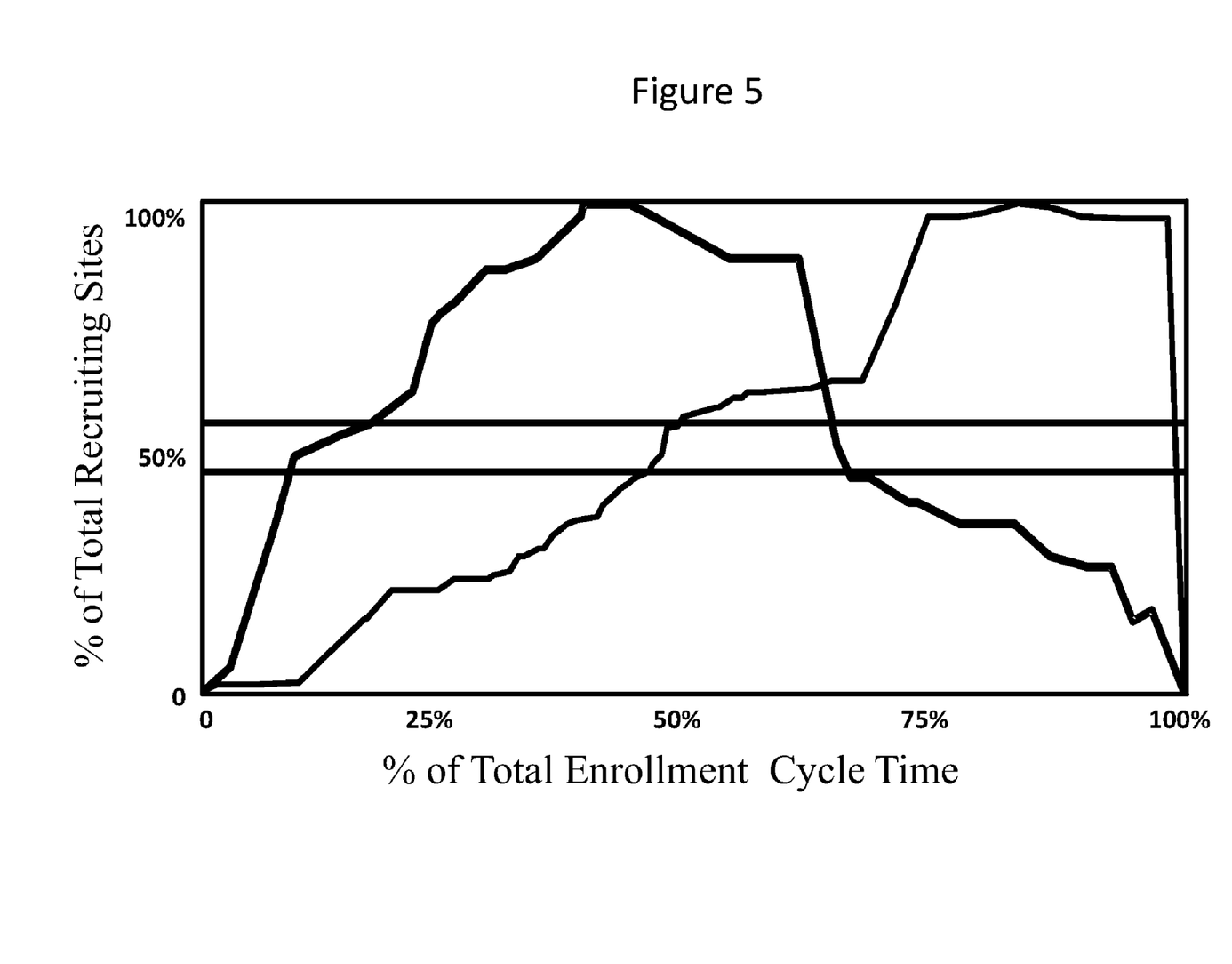
FIG. 5 shows when the site activation curves for clinical trials A and B were normalized and depicted on the same chart, the difference in SEI becomes quantifiable, and helps to find reasons that caused the difference.

The two straight lines tell us that more than half of the Clinical Trial A's 44 sites' enrollment capacities were utilized, compared to less than half of Clinical Trial B's 204 sites' enrollment capacities. Using a specific mathematical formula, one can calculate the Site Effectiveness Index (SEI) is 0.55 for Clinical Trial A, and 0.45 for Clinical Trial B. That means that if one were able to improve site activation in Clinical Trial B to be as good as in Clinical Trial A, one would need only 167 sites to get the same job done, instead of 204 sites. That is a reduction of 18 percent of the sites selected.

Measuring Site Enrollment Performance

Even with improved site activation, Clinical Trial B uses many more sites (167 vs. 44), and significantly longer enrollment duration (13 months vs. 9 months) than Clinical Trial A. If we look at the above study and this time consider a hypothetically modified Clinical Trial B—call it Clinical Trial BM—reaching a maximum number of sites activated in 7.5 months instead of the original 10 months. That brings the SEI up from 0.45 (Clinical Trial B) to 0.55 (Clinical Trial BM), the same as in Clinical Trial A. As shown in the figure below, the total chart area beneath the straight lines then becomes the same (see FIG. 6).

Figure 6:
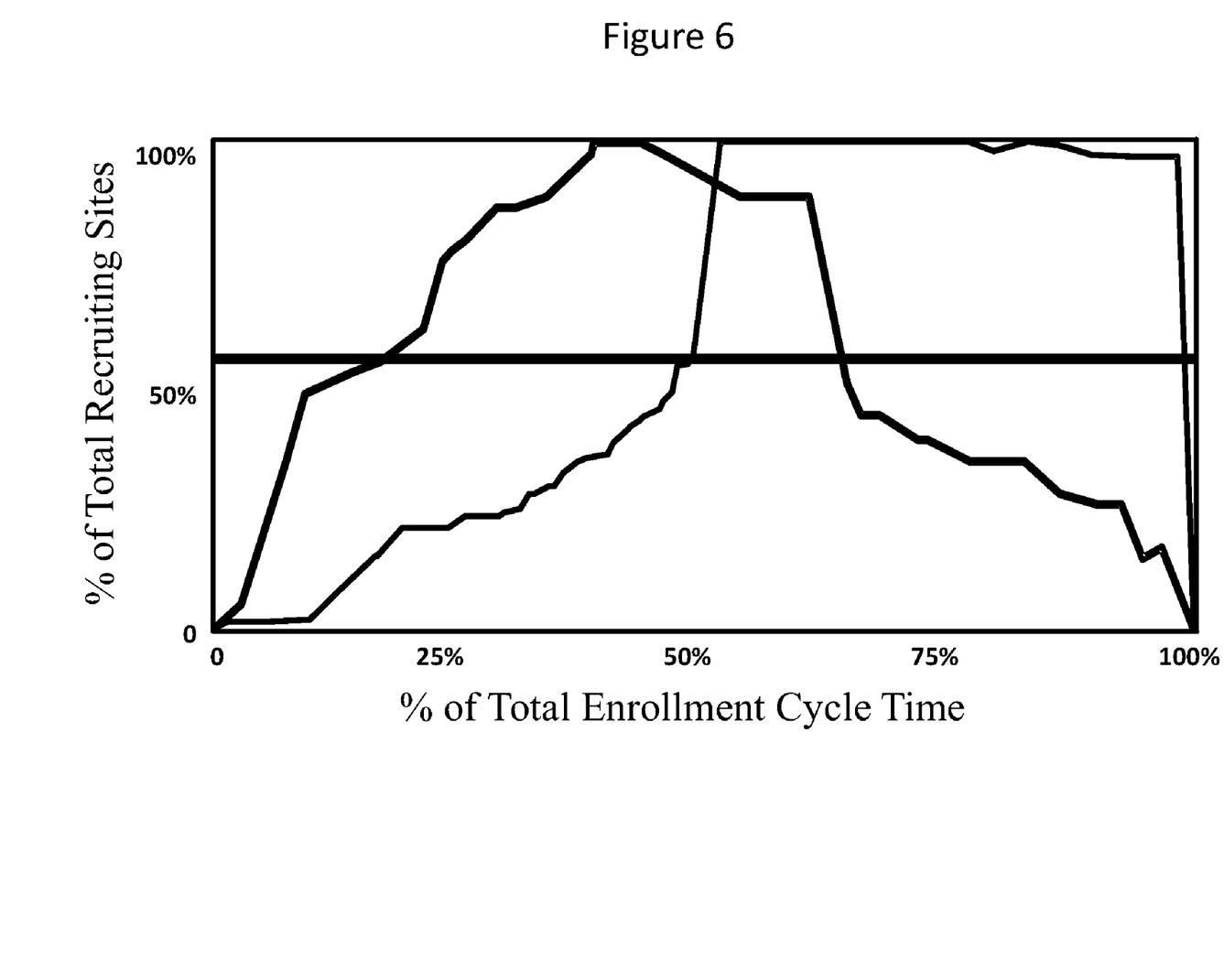
FIG. 6 shows specifically how SEI in Clinical Trial B can be improved to match that in Clinical Trial A, with reduced number of sites and shortened cycle time.

As noted above, improvement in site activation can reduce the total number of sites needed from 204 in Clinical Trial B to 167 in Clinical Trial BM. But 167 sites, 13 months, and 565 patients is still quite different from the 44 sites, 9 months, and 700 patients in Clinical Trial A. The 44 sites in Clinical Trial A, on average, performed much better in enrollment than those in Clinical Trial BM. When we calibrate the TRUE sites by the SEI of 0.55 for both Clinical Trial A and Clinical Trial BM, it gives 92 sites (167 sites×0.55) for Clinical Trial BM and 24 sites (44 sites×0.55) for Clinical Trial A. Therefore, the Average Site Enrollment Rate (ASER) is 3 patients per site per month (700 patients/24 sites/9 months) for Clinical Trial A, whereas ASER is 0.5 patients per site per month (565 patients/92 sites/13 months) for Clinical Trial B.

In other words, Average Sites Enrollment Rate (ASER) is independent of clinical trial enrollment duration. For example, if you have four sites opened for enrollment for one, three, five, and seven months, respectively, and enrolled 160 patients in total, the ASER for the four sites is 2.5 patients/site/month (160 patients/4 sites/(1+3+5+7) months). The enrollment cycle time for this clinical trial could be 7 months or 10 months, or even longer—the ASER for the four sites remains 2.5 patients/site/month. Generally speaking, it is safe to assume that the site opened for enrollment for seven months is likely the best performer among all the four sites.

Now we can see the picture more clearly: If we were able to select the same number of high enrolling sites in Clinical Trial B as we did in Clinical Trial A, we would only need 34 sites to enroll 565 patients (34 sites=204 sites×0.5 patients per site per month/3 patients per site per month) in 13 months. In other words, the enrollment performance (ASER) of the sites in Clinical Trial B and divide that by the enrollment performance (ASER) of the sites selected in Clinical Trial A, that is the portion of the 204 sites needed, which equals to 34 sites.

By now, we can see the financial consequences caused by the differences in site activation effectiveness and site enrollment performance. Assuming the cost to activate a site is $20,000 (a representative yet conservative industry estimate), needing 160 more sites in Clinical Trial B compared to Clinical Trial A means $3.2 million more in site activation costs. Assuming a site management fee is $1,500 per site per month, and the study duration is 8 months, there would be $1.9 million more in site management spending for Clinical Trial B. By adding the extra site activation fees and extra site management fees together, the cost comes to a hefty sum of $5.1 million.

Clinical Trial Planning

Incorporating this type of analysis in the clinical trial planning stage enables project teams to define operational boundaries on performance, set realistic time lines, and understand important trade-offs between the number of sites selected versus the number of monitoring resources needed to activate and manage those sites. This helps teams quantitatively identify improvement opportunities in their site selection and start-up processes. Then, when setting performance targets, we can invite all the stakeholders to go through individual parameters to reach consensus based on a common understanding, and align actions/resources to ensure total organizational support in reaching the performance targets.

For example, determining the targeted number of patients per site is generally about determining how many sites to use. The approach described herein assesses the issue from the perspective of site activation and enrollment performance. High priority clinical trials generally obtain more resources and financial support. However, effectively utilizing those allocated resources is an entirely different issue. As we saw in the earlier example, more money and resources (applied to activating more sites over a longer period of time) did not, in fact, shorten the enrollment cycle time—instead it prolonged it.

If we were able to get data from several dozen clinical trials in a single indication and enroll the same number of patients in each trial, we could look directly at the relationship between the number of sites used and the performance of those sites using Average Site Enrollment Rate (ASER). In reality, we use number of patients per site (Total Enrollment Target/Number of Sites) as a surrogate to number of sites in trials with same enrollment target.

By doing so, we minimize the impact of clinical trials with different enrollment targets, and still are able to understand the impact of number of sites being used when other factors are equal. We found that when number of patients enrolled per site increases, we increase the performance of all the deployed sites in that clinical trial, as measured by Average Site Enrollment Rate (ASER). In other words, by adding more sites to a clinical trial, the result is a reduction in the average performance of the sites the sponsor has activated. If the same number of patients are allocated across MORE sites then each site enrolls fewer patients and the Average Site Enrollment Rate (ASER) goes down.

Sponsors can rely on this approach to find the "Sweet Spot", with just the right amount of sites to ensure targeted enrollment cycle time to maximize the value of available resources against "speed to market' projections. For example, when working on a respiratory disease clinical trial, we find the ASER for clinical trials with biological intervention to be 0.52, versus 0.83 for the clinical trials with small molecule intervention.

This difference is highly instructive to sponsors as it anticipates and reflects the higher level of difficulties for sites to enroll patients in clinical trials with biological interventions for a particular disease. That 60 percent difference between 0.52 and 0.83 is significant enough to guide the sponsor to commit to a larger number of sites being deployed in a biological trial, so that targeted enrollment cycle times can be achieved.

As these parameters are objective and specific, they are easily accepted by project teams and provide a measure of objective performance to senior management. In return, it effectively improves communication and understanding among stakeholders as to the ramifications of selecting more or fewer sites for example.

This approach also provides a structured framework to proactively detect as well as manage possible derailments in the execution of the trial. Root causes for these derailments can be identified in specific areas, such as site activation and/or site enrollment performance. Before merely adding on more sites, study teams can seriously evaluate whether it makes more sense to enhance the enrollment performance of the existing sites (using a variety of methods and approaches), deploy a site activation "SWAT" team to rapidly activate any new sites or at least understand the time line implications of following their traditional site activation process.

What is claimed is:

1. A computer-based method of improving operational effectiveness for a clinical trial in planning, wherein a computer-based calculating system performs the processes of:
   (i) inputting historical clinical trial operation data for a disease condition from different clinical trials, wherein said historical clinical trial operation data for each single trial of said different clinical trials comprise date site i closed for patient enrollment (Eti), date site i opened for patient enrollment (Sti), maximum number of sites (N) opened for enrollment in the duration of patient enrollment at the study level, date clinical trial closed for patient enrollment (Ets), and date clinical trial opened for patient enrollment (Sts);
   (ii) normalizing said data from different clinical trials;
   (iii) calculating Site Effectiveness Index (SEI) for said normalized data using said computer-based calculating system, wherein the SEI is defined as $$SEI = \frac{\int_{i=1}^{N}(Et_i - St_i)}{(Et_s - St_s) \times N};$$

and
   (iv) analyzing and identifying clinical trials based on said calculated SEIs, wherein clinical trial practices of the identified clinical trials could be used to improve operational effectiveness of a clinical trial in planning.

2. The method of claim 1, wherein the historical data comprise parameters selected from the group consisting of number of investigator sites open for patient enrollment, design of the study, key inclusion exclusion criteria, targeted number of patient enrollment, company sponsoring the clinical trial, intervention(s), disease condition(s), and protocol identification(s) from sponsor(s).

3. The method of claim 1, wherein the normalization of data comprises expressing enrollment time as percentage of total enrollment cycle time.

4. The method of claim 1, wherein the normalization of data comprises expressing number of sites activated for enrollment as percentage of maximum number of sites open for enrollment.

5. The method of claim 1, wherein the SEI is related to Enrollment Cycle Time as follows: Enrollment Cycle Time=Total Enrollment/(Average Site Enrollment Rate) (SEI×N).

6. The method of claim 5, wherein the Average Site Enrollment Rate is defined as $$ASER = \frac{TE}{\int_{i=1}^{N}(Et_i - St_i)},$$

wherein TE is Total Enrollment.

7. The method of claim 1, wherein the SEI is calculated by measuring an area covered by a site activation curve.

8. The method of claim 7, wherein the area covered by a site activation curve is calculated as percentage of a rectangle area, wherein one side of the rectangle area equals to enrollment duration, and the other side equals to maximum number of sites open for enrollment.

9. The method of claim 1, wherein the SEI is expressed as a percentage ranging between 0% and 100%, exclusively.

* * * * *